(12) United States Patent
Kameyama et al.

(10) Patent No.: US 12,708,277 B2
(45) Date of Patent: Aug. 18, 2026

(54) PULSE WAVE DETECTION DEVICE

(71) Applicant: Taiyo Yuden Co., Ltd., Tokyo (JP)

(72) Inventors: Aiki Kameyama, Takasaki (JP); Katsuhiro Oyama, Takasaki (JP)

(73) Assignee: TAIYO YUDEN CO., LTD., Tokyo (JP)

( * ) Notice: Subject to any disclaimer, the term of this patent is extended or adjusted under 35 U.S.C. 154(b) by 43 days.

(21) Appl. No.: 18/786,972

(22) Filed: Jul. 29, 2024

(65) Prior Publication Data

US 2026/0026700 A1 Jan. 29, 2026

Related U.S. Application Data

(63) Continuation of application No. PCT/JP2022/043573, filed on Nov. 25, 2022.

(30) Foreign Application Priority Data

Jan. 31, 2022 (JP) ................................ 2022-013623

(51) Int. Cl.
*A61B 5/024* (2006.01)
*A61B 5/00* (2006.01)

(52) U.S. Cl.
CPC .......... *A61B 5/02427* (2013.01); *A61B 5/681* (2013.01)

(58) Field of Classification Search
CPC ............................ A61B 5/02427; A61B 5/681
See application file for complete search history.

(56) References Cited

U.S. PATENT DOCUMENTS

| | | | | |
|---|---|---|---|---|
| 10,448,848 | B2 * | 10/2019 | Park | A61B 5/7271 |
| 2001/0056243 | A1 * | 12/2001 | Ohsaki | G04G 21/025 600/503 |
| 2002/0188210 | A1 * | 12/2002 | Aizawa | A61B 5/02433 600/502 |

(Continued)

FOREIGN PATENT DOCUMENTS

| | | |
|---|---|---|
| JP | 2013-157 | 1/2013 |
| JP | 2013-063203 | 4/2013 |

(Continued)

OTHER PUBLICATIONS

International Search Report cited in PCT/JP2022/043573, mailed Feb. 14, 2023.

*Primary Examiner* — Seung C Sohn
(74) *Attorney, Agent, or Firm* — CHIP LAW GROUP

(57) ABSTRACT

Provided is a pulse wave detection device including a sensor substrate having a mounting surface and a back surface, a light receiving element disposed on the mounting surface of the sensor substrate, a light emitting element disposed on the mounting surface, and a light guide part having a first opening that surrounds the light receiving element, a second opening that corresponds to the first opening and is provided at a top part of a curved surface or in a vicinity of the top part, a third opening that surrounds the light emitting element, a fourth opening that corresponds to the third opening and is provided in the curved surface, a first light guide path having a reflective surface that couples the first opening with the second opening, and a second light guide path having a reflective surface that couples the third opening with the fourth opening.

6 Claims, 12 Drawing Sheets

(56) References Cited

U.S. PATENT DOCUMENTS

| | | | | |
|---|---|---|---|---|
| 2012/0150047 | A1* | 6/2012 | Terumoto | A61B 5/02427 600/479 |
| 2015/0112207 | A1 | 4/2015 | Inoue | |
| 2016/0120421 | A1 | 5/2016 | Matsuo | |
| 2022/0071561 | A1 | 3/2022 | Ajima | |

FOREIGN PATENT DOCUMENTS

| | | |
|---|---|---|
| JP | 2015-016194 | 1/2015 |
| JP | 2015-80601 | 4/2015 |
| JP | 2016-2167 | 1/2016 |
| JP | 2019-136441 | 8/2019 |
| JP | 2020-99603 | 7/2020 |

* cited by examiner

FIG. 14

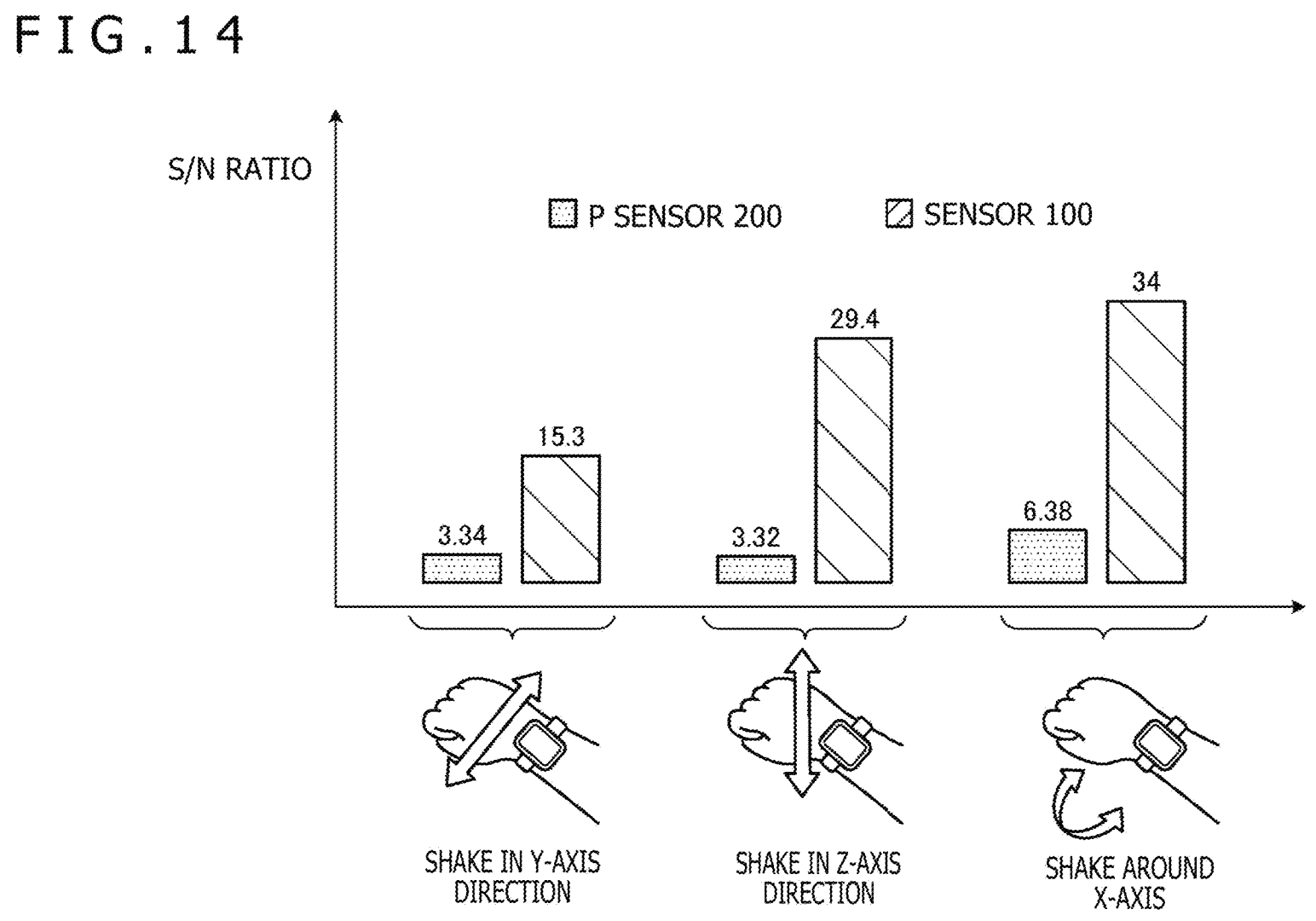

S/N RATIO

P SENSOR 200

SENSOR 100

3.34

15.3

3.32

29.4

6.38

34

SHAKE IN Y-AXIS DIRECTION

SHAKE IN Z-AXIS DIRECTION

SHAKE AROUND X-AXIS

PULSE WAVE DETECTION DEVICE

BACKGROUND

The present embodiment relates to a pulse wave detection device.

As one of kinds of pulse wave detection device, a photoelectric pulse wave sensor is known. The photoelectric pulse wave sensor irradiates a human body surface with light emitted by a light emitting element and receives transmitted light or reflected light. The wavelength of the light to be used is selected from a wavelength band having such characteristics as to be readily absorbed by blood hemoglobin (for example, a wavelength band from green to near-infrared). The photoelectric pulse wave sensor detects the pulse wave by using the fact that change in the amount of received light corresponds to the plethysmogram of the blood vessel.

Examples of the related art are disclosed in Japanese Patent Laid-Open Nos. 2013-63203 and 2015-16194.

SUMMARY

In recent years, the photoelectric pulse wave sensor has been often mounted on a wearable device such as a smartwatch. In such a case, it is desired to stably detect the pulse wave with high sensitivity.

There is a need for provision of a pulse wave detection device capable of stable pulse wave detection with high sensitivity.

According to an embodiment of the present disclosure, a pulse wave detection device has a sensor substrate having a mounting surface and a back surface, a light receiving element disposed on the mounting surface of the sensor substrate, and a light emitting element disposed on the mounting surface separately from the light receiving element. The pulse wave detection device has also a light guide part having, on the side of the mounting surface of the sensor substrate, a first opening that surrounds the light receiving element, a second opening that corresponds to the first opening and is provided at a top part of a curved surface or in the vicinity of the top part, a third opening that surrounds the light emitting element, a fourth opening that corresponds to the third opening and is provided in the curved surface, a first light guide path having a reflective surface that couples the first opening with the second opening, and a second light guide path having a reflective surface that couples the third opening with the fourth opening.

According to an embodiment of the present disclosure, an effect that a pulse wave detection device capable of stable pulse wave detection with high sensitivity can be provided is achieved.

BRIEF DESCRIPTION OF THE DRAWINGS

FIG. 14 is a diagram illustrating a signal-to-noise (S/N) ratio when a user who wears the wearable device equipped with the sensor of the embodiment in which the second surface is formed of a curved plane shakes an arm in various directions;

DETAILED DESCRIPTION OF THE PREFERRED EMBODIMENT

First, a problem of a photoelectric pulse wave sensor in the past will be described. The photoelectric pulse wave sensor in the past will be given a character "P" from a word "prior" and be represented as a P sensor 200 hereinafter. In the present specification, a term "return light" refers to light for pulse wave detection that has been applied to a human body and returned from the human body. Furthermore, in the present specification, description will be made about the cases in which the P sensor 200 and a pulse wave detection device (referred to also as a sensor) of an embodiment are mounted on a wristwatch-type wearable device (for example, smartwatch).

Figure 1:
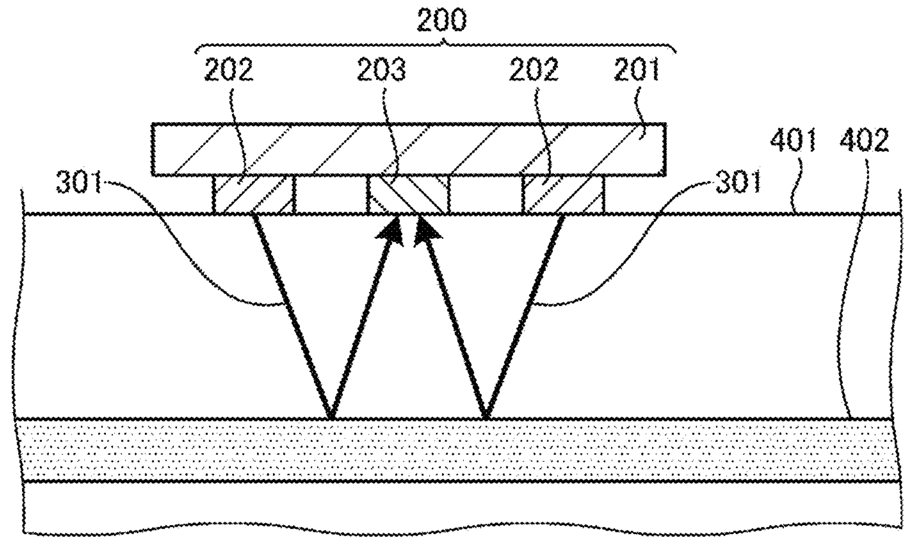
FIG. 1 is a diagram that illustrates a sensor in the past and is for explaining optical paths of light for pulse wave detection.
Figure 2:
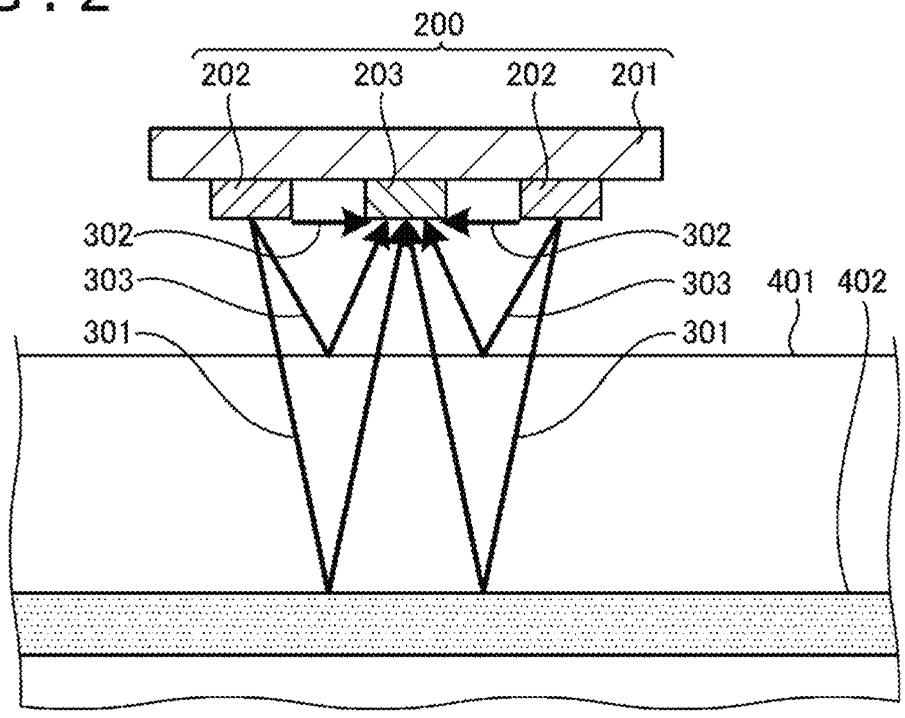
FIG. 2 is a diagram that illustrates the sensor in the past and is for explaining the optical paths of the light for pulse wave detection.

FIGS. 1 and 2 are diagrams that illustrate the P sensor 200 and are for explaining the optical paths of the light for pulse wave detection.

In FIG. 1, a skin 401 of an arm and a blood vessel 402 under the skin 401 are illustrated. The P sensor 200 includes a sensor substrate 201, two light emitting elements 202, and a light receiving element 203. The two light emitting elements 202 and the light receiving element 203 are mounted on a surface of the sensor substrate 201. The P sensor 200 is disposed in such a manner that the sensor surface is in tight contact with the skin 401.

The light received by the light receiving element 203 is mainly light 301 that has been emitted from the light emitting element 202 and has entered the region under the skin 401 and has returned through reflection or scattering by tissue under the skin. Because the blood vessel 402 exists under the skin, part of the light 301 is affected by the plethysmogram of the blood vessel 402 and increases or decreases. In particular, oxidized hemoglobin exists in the blood of the artery and has a characteristic of absorbing incident light. Therefore, a pulse wave signal can be measured by sensing the blood flow rate (change in the volume of the blood vessel) that changes in association with the pulsation of the heart in a time-series manner.

Thus, the P sensor 200 can detect the pulse wave on the basis of change in the amount of light 301.

However, when the P sensor 200 is mounted on a wristwatch-type wearable device, it is often difficult to bring the sensor surface into tight contact with the skin 401 depending on the method for wearing on an arm and the shape of the arm of the wearing person. Moreover, due to body motion of the wearing person, it is often difficult to continue to bring the sensor surface into tight contact with the skin 401 during the period of detection of the pulse wave. In these cases, a gap is often generated between the sensor surface of the P sensor 200 and the skin 401.

FIG. 2 illustrates a case in which a gap has been generated between the skin 401 and the sensor surface and illustrates optical paths in this case.

As illustrated in FIG. 2, the light receiving element 203 receives light 302 directly incident on the light receiving element 203 from the light emitting element 202 and light 303 that is reflected or scattered by the surface of the skin 401 to return, besides the light 301 that enters the region under the skin 401 and returns through reflection or scattering at a site at which the blood vessel 402 exists. The light 302 and the light 303 are not affected by the plethysmogram of the blood vessel 402. In the case illustrated in FIG. 2, the ratio of components having no relation to the pulse wave like the light 302 and the light 303 becomes high compared with the case illustrated in FIG. 1. Thus, the S/N ratio of the pulse wave waveform obtained by calculation deteriorates and the detection of the pulse wave becomes difficult.

The pulse wave detection device of the embodiment suppresses the incidence of the light 302 and the light 303 on the light receiving element by a light guide part and thereby enables stable pulse wave detection with high accuracy.

The pulse wave detection device of the embodiment will be described in detail below. Note that the present disclosure is not limited by this embodiment. Furthermore, the description will be made on the basis of the assumption that the pulse wave detection device of the embodiment is mounted on a wristwatch-type wearable device as described above. The pulse wave detection device of the embodiment may be mounted on a wearable device other than the wristwatch type. For example, the pulse wave detection device of the embodiment can be mounted on a wearable device such as smartglasses, a smart ring, or a wireless earphone. In the case of smartglasses, the sensor surface can be disposed on a nose pad, an ear hook part, or other parts. Furthermore, the pulse wave detection device of the embodiment may be mounted on an optional stationary-type device. For example, the pulse wave detection device can be mounted on an inspection device that measures the cardio-ankle vascular index (CAVI) or the ankle-brachial pressure index (ABI), a flow mediated dilation (FMD) inspection device, or other devices.

Figure 3:
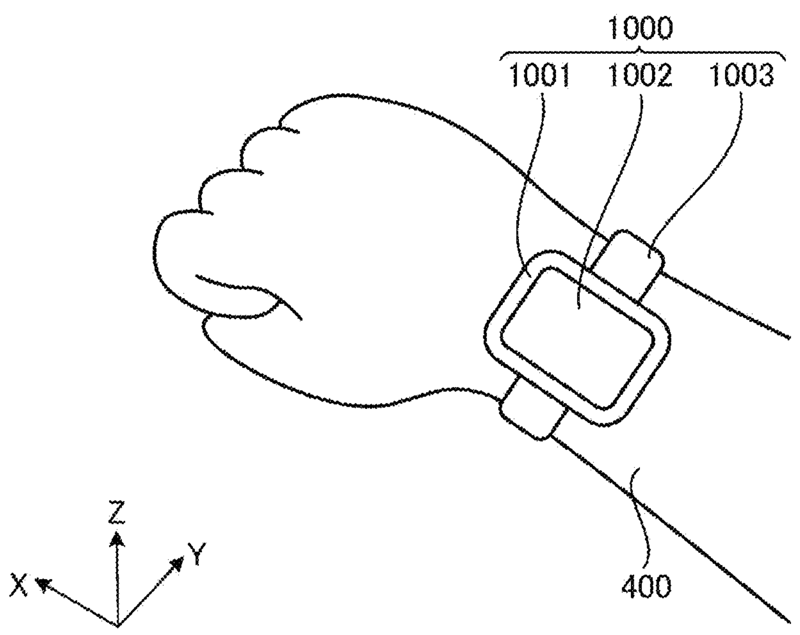
FIG. 3 is a diagram for explaining a wearing method of a wearable device on which a pulse wave detection device of an embodiment is mounted.

FIG. 3 is a diagram for explaining a wearing method of a wearable device 1000 on which the pulse wave detection device of the embodiment is mounted.

The wearable device 1000 includes a casing 1001 with a flattened shape, a display device 1002, and a band 1003. The casing 1001 is composed of an upper surface, a lower surface, and side surfaces that couple the circumference of the upper surface and the circumference of the lower surface. In the diagram, the casing 1001 is a casing formed of a substantially rectangular parallelepiped and includes four side surfaces.

A sensor 100 is disposed on the casing 1001. The band 1003 is attached to one side surface of the casing 1001 and the side surface thereof on the opposite side. The band 1003 is wound around an arm 400 of a wearing person, and thereby the lower surface of the casing 1001 is fixed to the arm 400. The display device 1002 is disposed on the surface (upper surface) on the opposite side to the surface facing the arm 400 in the casing 1001. The wearable device 1000 outputs various pieces of image information to the display device 1002. The wearing person can visually check the various pieces of image information output to the display device 1002.

Note that, hereinafter, description will be made in such a manner that the direction corresponding to the direction along which the arm extends is defined as the positive direction of an X-axis and the direction from the lower surface toward the upper surface in two surfaces of the casing 1001 is defined as the positive direction of a Z-axis and the axis orthogonal to both the X-axis and the Z-axis is defined as a Y-axis.

Figure 4:
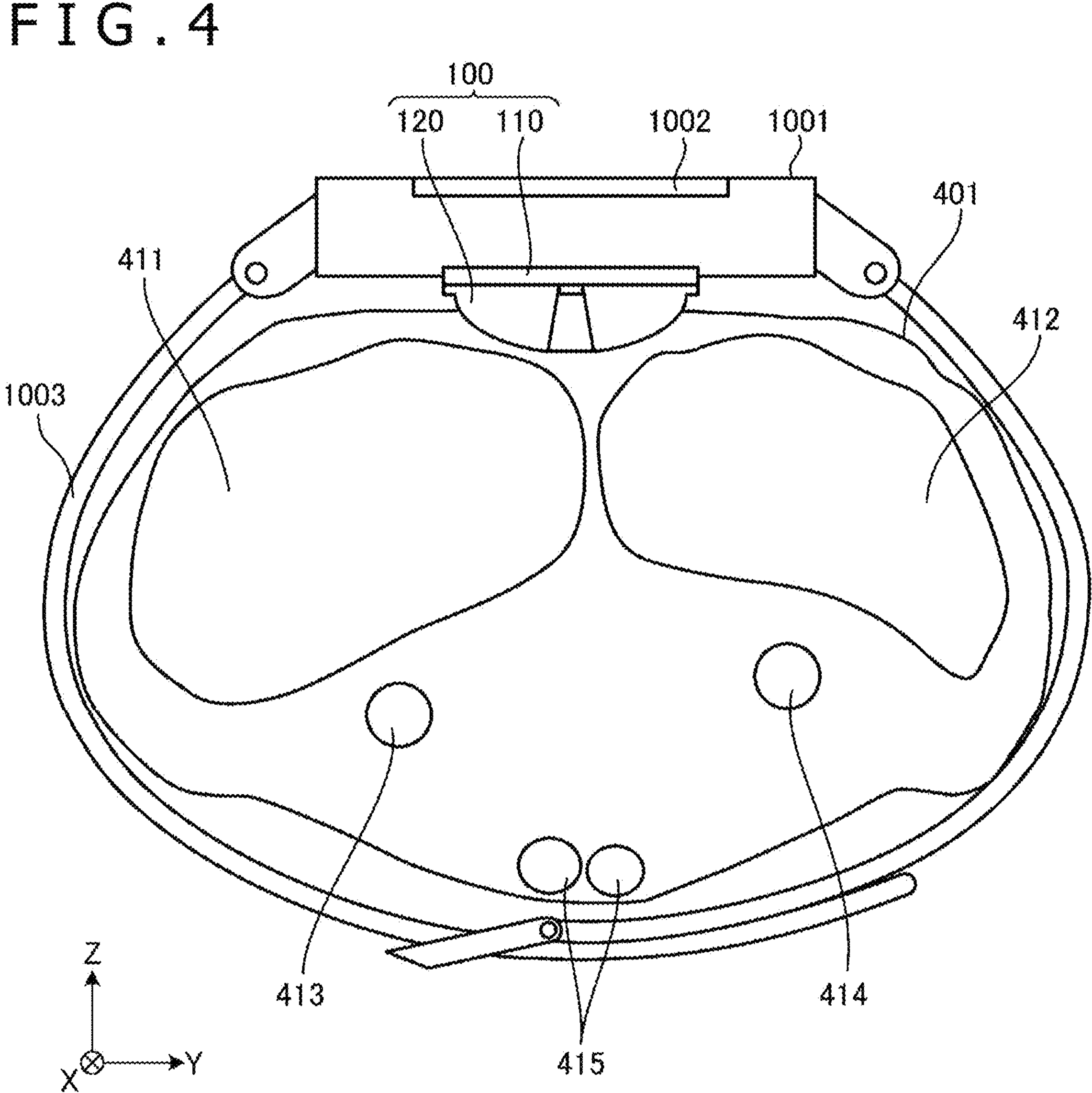
FIG. 4 is a sectional view obtained by cutting, by a YZ-plane, the wearable device of the embodiment in a state in which it is worn on an arm.

FIG. 4 is a sectional view of the wearable device 1000 and the arm 400 in a YZ-plane in FIG. 3.

Inside the arm 400, a radius 411 and an ulna 412 extend along the X-axis direction. A radial artery 413 runs below the radius 411, and an ulnar artery 414 runs below the ulna 412. A tendon 415 runs through a region under the skin on the lowermost side in the section of the arm 400.

The sensor 100 that is the pulse wave detection device of the embodiment is disposed on the lower surface of the casing 1001. This sensor 100 includes a sensor substrate 110 and a light guide part 120.

Figure 5:
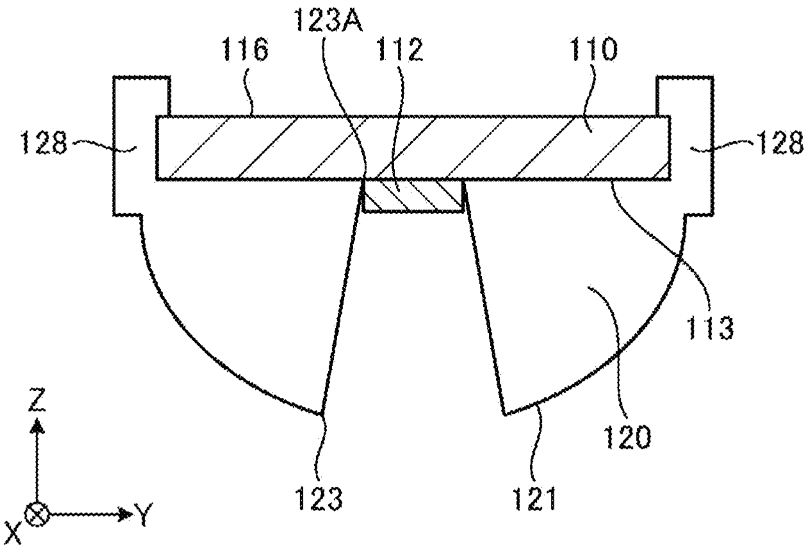
FIG. 5 is a sectional view obtained by cutting a sensor of the embodiment by a YZ-plane.
Figure 6:
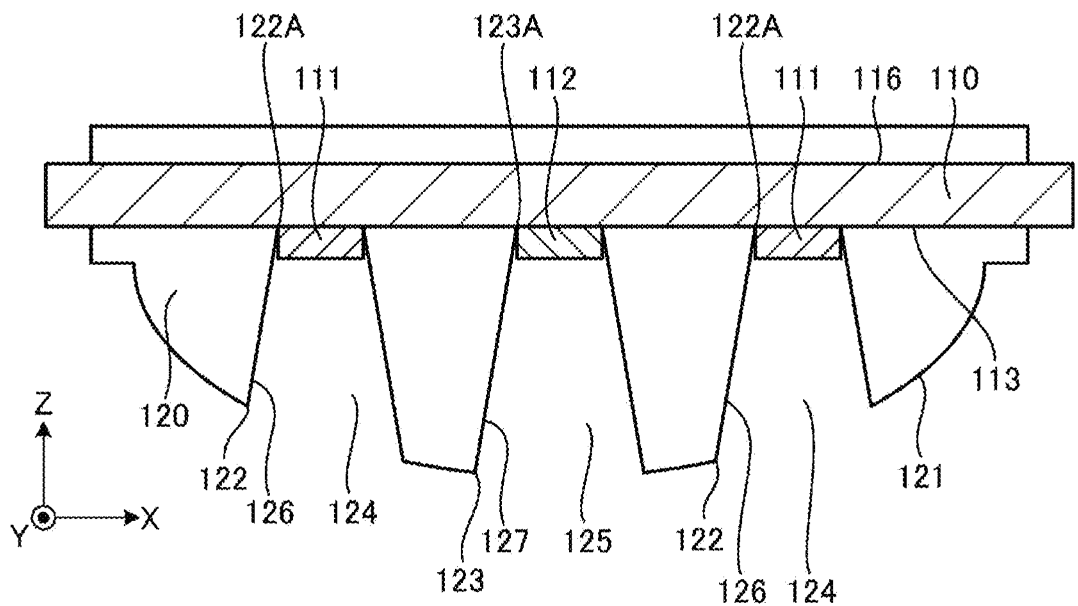
FIG. 6 is a sectional view obtained by cutting the sensor of the embodiment by an XZ-plane.

FIGS. 5 and 6 illustrate the sensor 100 in the same orientation as that of FIG. 4.

Two light emitting elements 111 (not illustrated in FIG. 5) and a light receiving element 112 are disposed on the surface of the sensor substrate 110 on the negative side in the Z-axis direction, that is, a mounting surface 113 of elements.

Furthermore, the light guide part 120 is disposed on the mounting surface 113 of the sensor substrate 110 in such a manner as to encompass and cover the light emitting elements 111 and the light receiving element 112. Note that the mounting surface 113 of the sensor substrate 110 is one example of a first surface (first surface 113 to be described later). Note that the surface facing the mounting surface 113 in the sensor substrate 110 will be referred to as a back surface.

Figure 8:
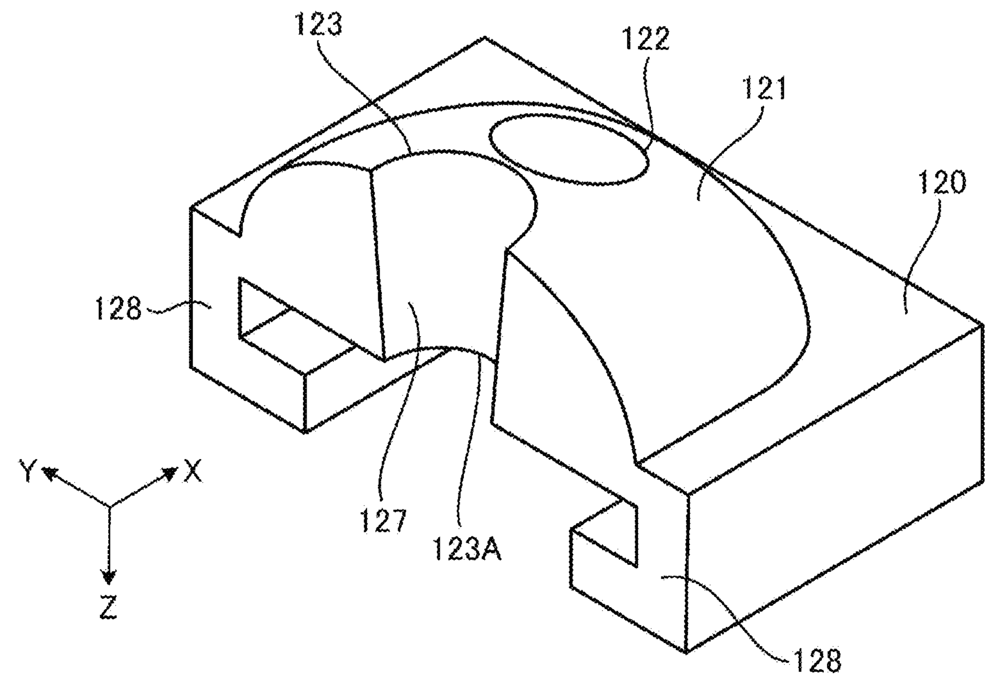
FIG. 8 is a perspective view of a light guide part of the embodiment cut by a YZ-plane.

Referring to FIG. 4, the width of the light guide part 120 in the Y-axis direction is sufficiently smaller than the width of the arm 400 in the Y-axis direction. Moreover, the light guide part 120 protrudes toward the arm from the mounting surface of the casing 1001. Actually, this protruding surface has a form like one obtained by cutting a sphere or rugby ball as illustrated in FIG. 8, and a section thereof forms a curved surface as illustrated in FIGS. 5 and 6.

Thus, when the wearable device 1000 is worn on the arm 400, depending on the degree of tightening of the band 1003, part of the light guide part 120 bites into the arm 400 and the curved surface of the light guide part 120 gets tight contact with the skin. Note that the curved surface of the light guide part 120 is one example of a second surface (second surface 121 to be described later).

The light guide part 120 may be formed of an elastic body. The elastic body is composed of a material that can expand or contract when a force is applied thereto. The elastic body is, for example, silicone or rubber. However, it is not limited to them. Moreover, it is desirable that the elastic body forming the light guide part 120 be composed of a material with the following natures similarly to a rubber band of the smartwatch. Specifically, the material provides a good texture and allows the skin in contact to be less sweaty. Furthermore, the material provides a comfortable feeling of wearing and has high durability and exhibits a low likelihood of deformation and breakage.

Because being formed of the elastic body, the light guide part 120 can expand or contact when a force is applied thereto. Thus, the tight contact between the curved surface (that is, the second surface 121) of the light guide part 120, and the skin of the arm 400 improves. Even when the wearing position of the sensor 100 is displaced in the X-axis direction, the Y-axis direction, or the Z-axis direction depending on body motion of the wearing person or the wearing method or is somewhat displaced in a rotational direction around any of these axes, this displacement can be absorbed by the elastic deformation of the light guide part 120 and the tight contact between the curved surface (that is, the second surface 121) of the light guide part 120 and the skin can be kept.

Although it has been explained that the tight contact is obtained, the tight contact is not established if the degree of tightening of the band 1003 is low. When this wearable device 1000 is worn in such a manner that part of the protruding part abuts against or sinks into the skin when the wearable device 1000 is put on an arm by the band, it becomes possible to capture reflected light from the light guide part 120 even when this wearable device 1000 is displaced to a certain degree. Details will be described later.

Figure 7:
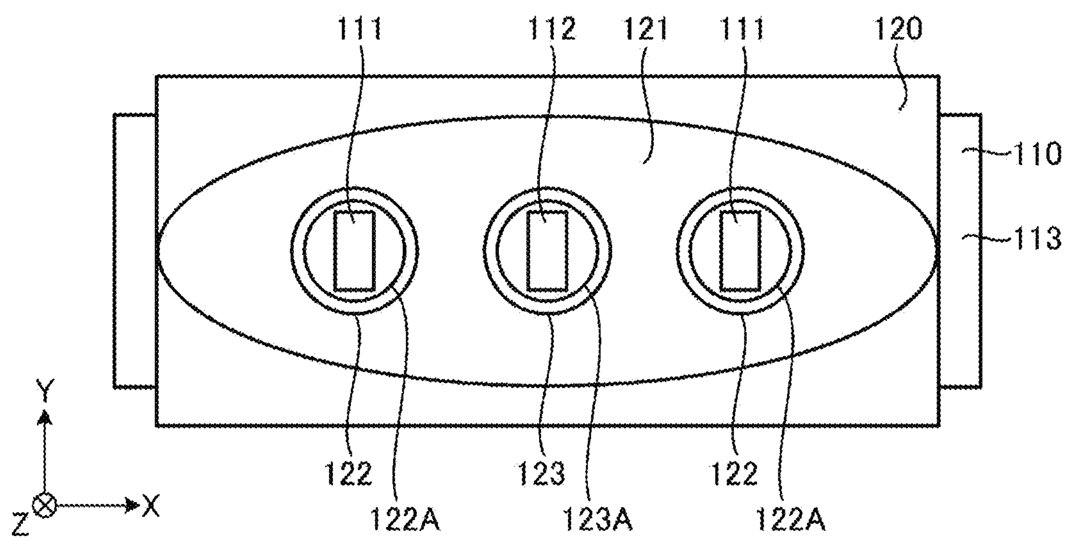
FIG. 7 is a diagram of the sensor of the embodiment as viewed from the negative side in a Z-axis direction.

FIG. 5 is a sectional view obtained by cutting the light receiving element 112 by a YZ-plane in FIG. 7. FIG. 6 is a sectional view obtained by cutting the light emitting elements 111 and the light receiving element 112 by an XZ-plane in FIG. 7. FIG. 7 is a plan view of the sensor 100 of the embodiment and is a diagram as viewed from the negative side in the Z-axis direction. FIG. 8 is a perspective view of the light guide part 120 of the embodiment cut by a YZ-plane.

As illustrated in FIGS. 5 to 7, the two light emitting elements 111 and the light receiving element 112 are disposed separately in the X-axis direction (long side direction) on the mounting surface 113 of the sensor substrate 110, that is, the surface 113 facing the skin 401. Moreover, the one light receiving element 112 is disposed between the two light emitting elements 111 on the surface 113. Hereinafter, the surface 113 will be represented as the first surface 113.

Each light emitting element 111 emits light in such a wavelength band as to be readily absorbed by hemoglobin. For example, this wavelength band is a wavelength band from green to near-infrared. The two light emitting elements 111 may emit light with the same wavelength or may emit light with wavelengths different from each other. Each light emitting element 111 is a light emitting diode, for example. Note that each light emitting element 111 does not need to be the light emitting diode.

The light receiving element 112 outputs a signal according to the amount of received light. The light receiving element 112 is a photodiode, for example. Note that the light receiving element 112 does not need to be the photodiode.

The curved surface 121 of the light guide part 120 has two first openings 122 for the light emitting element and one second opening 123 for the light receiving element. Note that the curved surface 121 will be represented as the second surface 121.

Figure 10:
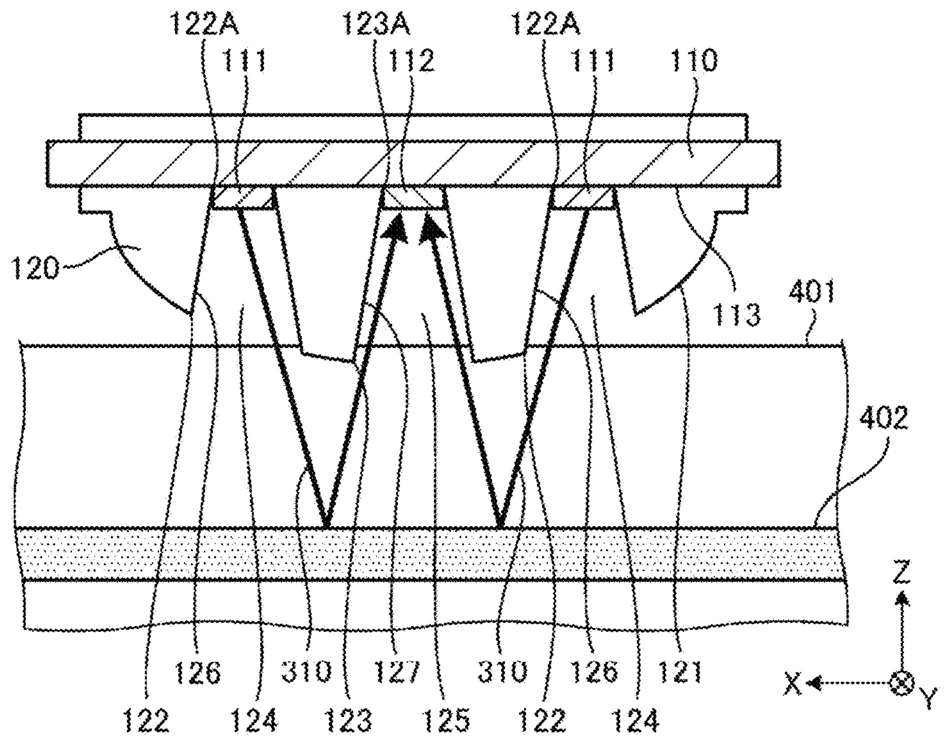
FIG. 10 is a diagram for explaining optical paths of light emitted from light emitting elements in the sensor of the embodiment in a case in which the wearable device is worn with a second surface in tight contact with the skin.

As illustrated in FIG. 10, the light guide part 120 has two first light guide paths 124 for the light emitting element and one second light guide path 125 for the light receiving element.

As illustrated in FIGS. 7 and 8, the light guide part 120 is a dome-shaped resin molded body and has the curved surface 121 and a flat abutting surface on the side of the sensor substrate 110.

The flat surface of the abutting surface is a rectangle (here, oblong) as illustrated in FIG. 7, and the curved surface 121 curves from the inside of the outer shape of the flat surface toward the outside. Because curving and protruding in such a manner as to collectively surround the two light emitting elements 111 and the light receiving element 112, the curved part exhibits an ellipsoidal shape as viewed in plan view.

Furthermore, openings 122A individually surrounding the two light emitting elements 111 and an opening 123A surrounding the light receiving element 112 are made in the abutting surface.

The periphery of each opening 122A forms a megaphone-shaped reflective surface that leads to the circumference of the corresponding first opening 122, and the inside of the reflective surface forms a space.

Part of light emitted from the light emitting element 111 straight travels in the space of the first light guide path 124 and is emitted to the external (skin). Furthermore, part of the light is emitted to the external while reflecting at the reflective surface of the first light guide path. Meanwhile, part of light that enters the second opening 123 of the second light guide path directly traves toward the light receiving element whereas part of the light travels toward the light receiving element while reflecting at the reflective surface of the second light guide path 125.

Note that the sensor substrate 110 is formed of a printed board composed of a resin or ceramic and is provided with an electrically-conductive pattern composed of electrodes and wiring lines disposed on the mounting surface side, and the light emitting elements and the light receiving element are mounted through being electrically connected to the electrodes. As insulation treatment, the light guide part 120 is composed of an insulator and the surface of the printed board is coated with solder resist. This allows the abutting surface of the light guide part 120 to abut against the printed board.

Each first light guide path 124 can guide light emitted from the light emitting elements 111 to the arm 400 when the wearable device 1000 is worn on the arm 400. Furthermore, the second light guide path 125 can guide return light from the arm 400 to the light receiving element 112.

As illustrated in FIGS. 5 to 8, each first light guide path 124 has a tapered shape in which the sectional area in the XY-plane becomes larger from the side of the sensor substrate 110 toward the side of the first opening 122. The second light guide path 125 has a tapered shape in which the sectional area in the XY-plane becomes larger from the side of the sensor substrate 110 toward the side of the second opening 123.

An inner wall 126 of each first light guide path 124 and an inner wall 127 of the second light guide path 125 have a structure to reflect light.

As described above, the light guide part 120 is molded with a resin mold. Thus, glossing treatment is executed for the inner surface of the mold corresponding to the inner walls 126 and 127. Thus, the light reflectance of the inner walls 126 and 127 improves and energy is not wastefully absorbed at the reflective surface. Therefore, the sensitivity of the pulse wave detection device improves. In particular, an epoxy resin or other materials are molded with glossiness. Thus, treatment such as plating is optional. On the other hand, the resin itself has light transmissibility although there is a difference in the degree thereof depending on the material. Thus, the inner walls 126 and the inner wall 127 may be coated with a material (for example, metal) that reflects light by plating, sputtering, vapor deposition, or other methods.

Due to allowing the inner walls 126 to have the structure to reflect light, light of the light emitting elements 111 can be guided to the external, and therefore the amount of light applied to the arm 400 can be increased. Moreover, due to allowing the inner wall 127 to have the structure for reflection, oblique light of return light from the arm can be guided to the light receiving element 112 by one or more times of reflection.

As illustrated in FIGS. 5 and 8, in the light guide part 120, the abutting surface on the side of abutting against the sensor substrate 110 is provided with folded-back parts 128 that extend from the sides corresponding to two opposed sides of the sensor substrate toward the back surface of the sensor substrate 110.

For example, at both ends of the light guide part 120 in the Y-axis direction, the folded-back parts 128 folded onto a back surface 116 (represented as third surface 116) of the sensor substrate 110 from the side surfaces of the long sides of the sensor substrate 110 are made. This folded-back part 128 has an abutting surface that abuts against the back surface of the sensor substrate 110 with a slight width from the circumference of the back surface. The sensor substrate 110 is formed of a printed board and therefore has a certain degree of flatness. Thus, by inserting and fitting the sensor substrate 110 into spaces existing at the folded-back parts 128 of the light guide part 120, the abutting surface of the light guide part 120 is made to abut against the mounting surface of the sensor substrate 110 and is fixed.

As illustrated in FIGS. 5 to 8, in the second surface 121 of the light guide part 120, the second opening 123 is formed at a top part of the curved part. That is, the second opening 123 is formed by a curved plane at the place with the maximum protrusion height.

Figure 9:
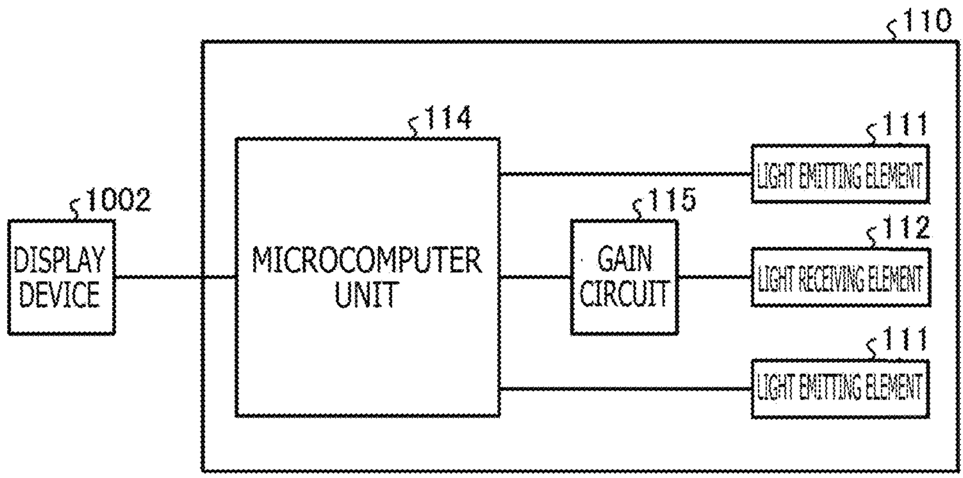
FIG. 9 is a block diagram for explaining a circuit mounted on a sensor substrate of the embodiment.

FIG. 9 is a block diagram for explaining a circuit mounted on the sensor substrate 110 of the embodiment.

The sensor substrate 110 has the two light emitting elements 111, the light receiving element 112, a microcomputer unit 114, and a gain circuit 115.

The gain circuit 115 is a circuit that amplifies a signal from the light receiving element 112.

The microcomputer unit 114 is a circuit including a processor and a memory. The processor is a central processing unit (CPU), for example.

Through execution of a program by the processor, the microcomputer unit 114 turns on the light emitting elements 111 and calculates the pulse wave on the basis of the signal from the light receiving element 112 that has received light through the gain circuit 115. The microcomputer unit 114 can display the pulse wave acquired by this calculation on the display device 1002.

Note that the sensor 100 described above includes the two light emitting elements 111 and the one light receiving element 112. The one light receiving element 112 is disposed at substantially the center of the first surface 113 of the sensor substrate 110, and the two light emitting elements 111 are separately disposed around the light receiving element 112. The sensor 100 may have three or more light emitting elements 111, and the light emitting elements 111 may be disposed around the light receiving element 112. At the position at which the light emitting element 111 is disposed, the light receiving element 112 may exist instead. In this case, at the position at which the light receiving element 112 is disposed, the light emitting element 111 may exist instead. The number of light emitting elements 111 included in the sensor 100 is not limited to two. Furthermore, the number of light receiving elements 112 included in the sensor 100 is not limited to one. Moreover, it suffices for the light guide part 120 to include the first openings 122 and the first light guide paths 124 in a number corresponding to the number of light emitting elements 111 and the second openings 123 and the second light guide paths 125 in a number corresponding to the number of light receiving elements 112.

As described above, according to the present embodiment, the sensor 100 includes the sensor substrate 110 and the light guide part 120. On the first surface 113, which is the mounting surface of the sensor substrate 110, the light emitting elements 111 that emit light and the light receiving element 112 that outputs a signal according to the amount of return light are disposed. The light receiving element 112 is disposed at a central part of the first surface 113 of the sensor substrate 110 and the two light emitting elements 111 are separately disposed around the light receiving element 112. The light guide part 120 is disposed on the first surface 113. The light guide part 120 has the second surface (curved surface) 121 that has the first openings 122 and the second opening 123 and that faces a human body and gets contact with the human body. The light guide part 120 has the first light guide paths 124 that lead to the first opening 122 from the light emitting element 111 and the second light guide path 125 that leads to the second opening 123 from the light receiving element 112. The microcomputer unit 114 is disposed on the sensor substrate 110 with electrical connection to the sensor substrate 110. The microcomputer unit 114 calculates the pulse wave on the basis of the signal output from the light receiving element 112.

Figure 12:
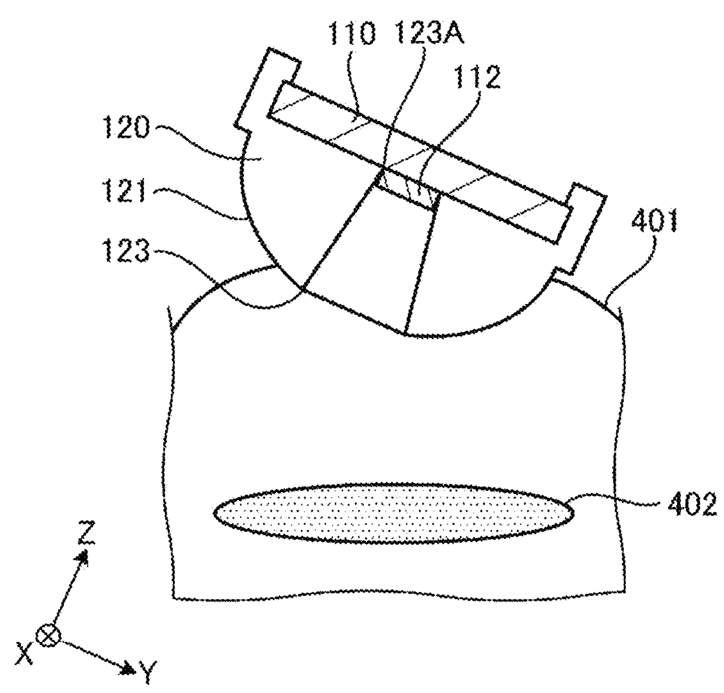
FIG. 12 is a diagram illustrating a state of contact between the light guide part of the embodiment and the skin in a case in which the contact direction tilts around an X-axis.
Figure 13:
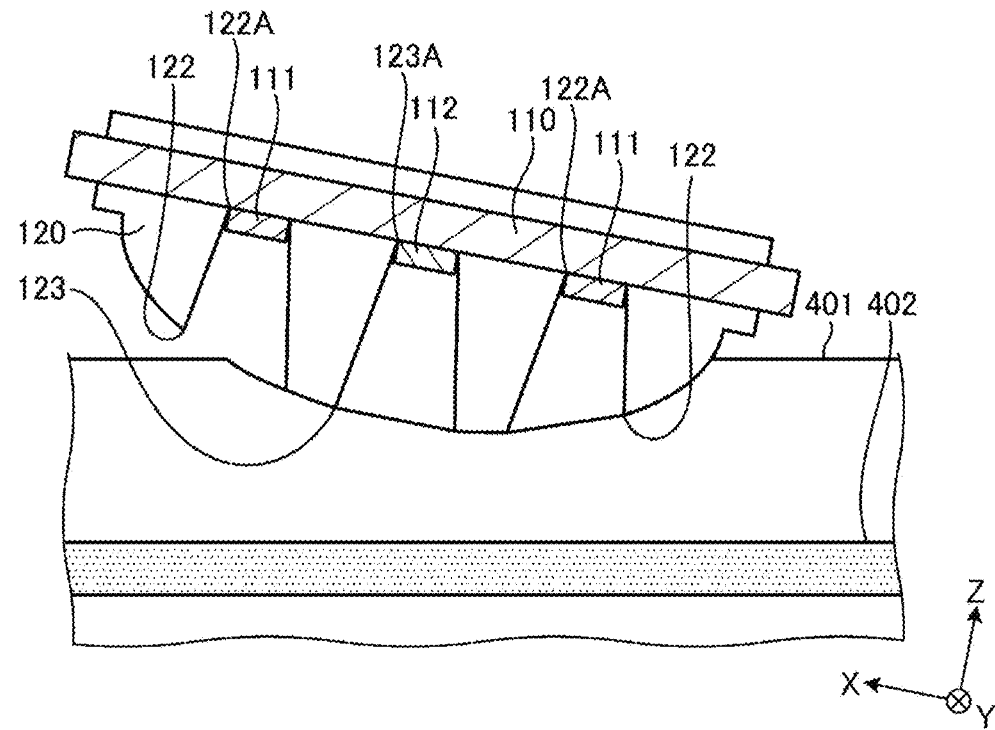
FIG. 13 is a diagram illustrating a state of the contact between the light guide part of the embodiment and the skin in a case in which the contact direction tilts around a Y-axis.

FIG. 10, 12, or 13 illustrates a case in which the wearable device 1000 is worn with the second surface (curved surface) 121 in tight contact with the skin.

Because being formed of the curved part, the light guide part 120 is displaced up, down, left, or right in such a manner that particularly the second opening 123 existing around the top part and the periphery thereof serve as a fulcrum. Thus, the peripheral part of the second opening 123 is in tight contact and ensures the optical path even when the light guide part 120 is displaced. Accordingly, most of the light that enters the second opening 123 is the return light.

In the light guide part 120, the first light guide paths 124 that guide light 310 from the light emitting element 111 and the second light guide path 125 that guides the return light that returns from the human body to the light receiving element 112 are made.

Thus, when the peripheral part of the second opening 123 is in tight contact with the skin 401, light from the light emitting element 111 enters the region under the skin, and the return light travels directly toward the light receiving element 112. Furthermore, noise light due to the existence of a gap as in FIG. 2 is blocked. In particular, light 310 that reflects at the skin 401 and travels toward the light receiving element 112 is blocked. Thus, noise components having no relation to the pulse wave can be significantly reduced, and therefore detection of the pulse wave with high accuracy is enabled.

Figure 11:
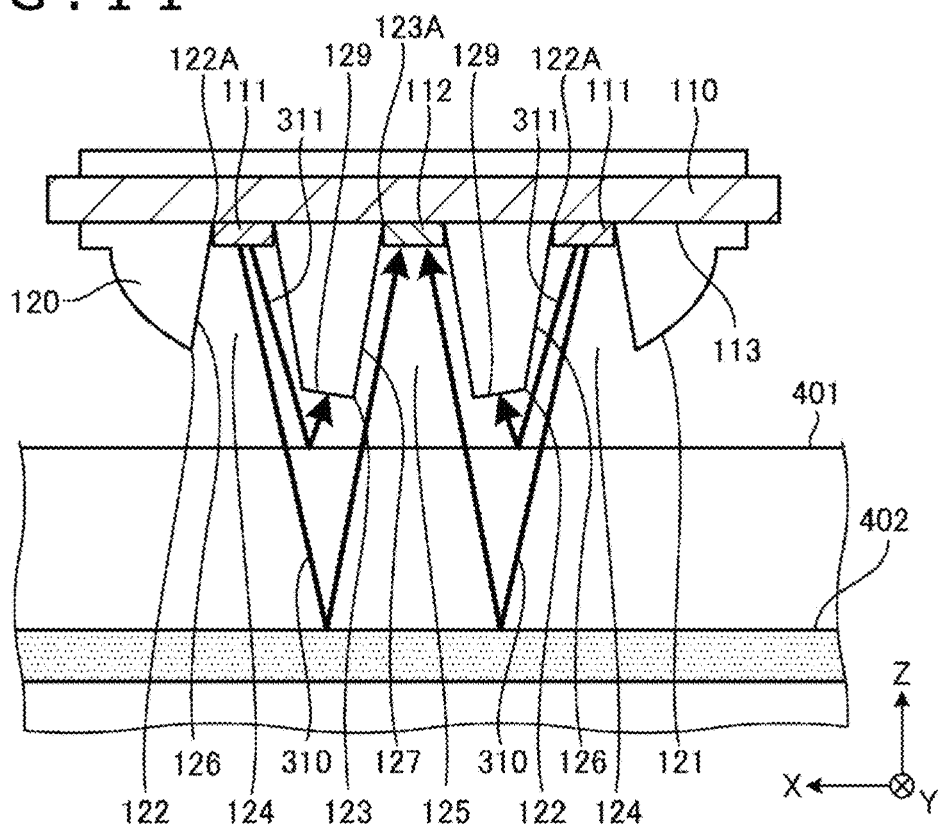
FIG. 11 is a diagram for explaining the optical paths of light emitted from the light emitting elements in the sensor of the embodiment in a case in which a gap has been generated between the second surface and the skin.

FIG. 11 illustrates a case in which a gap has been generated between the second surface 121 and the skin. However, in general, as illustrated in FIGS. 12 and 13, the wearable device 1000 is worn in such a manner that the curved surface typically abuts against the skin, and therefore a gap is not generated. Here, description will be made on the basis of the assumption that a gap has been generated.

As illustrated in FIG. 11, even if the gap has been generated between the second surface 121 and the skin 401, the light guide part 120 has its height at the curved surface protruding toward the skin. The place corresponding to this height serves as a barrier against light and can prevent the entry of light that becomes noise.

Moreover, according to the embodiment, the light guide part 120 is formed of an elastic body.

Thus, even when the wearing position of the sensor 100 is somewhat displaced in the X-axis direction, the Z-axis direction, or the Y-axis direction or around any of these axes depending on body motion of the wearing person or the wearing method, this displacement can be absorbed by the deformation of the light guide part 120, and the tight contact between the second surface 121 and the skin 401 can be kept. As described above, it becomes easy to keep the tight contact between the peripheral part of the second opening 123 as the top part and the skin 401. Thus, light 311 that is emitted from the light emitting element 111 and is reflected or scattered by the skin 401 to travel toward the light receiving element 112 can be blocked. As a result, stable pulse wave detection with high sensitivity is enabled.

Furthermore, because the part that gets contact with the skin of the wearing person is soft, a feeling of discomfort given to the wearing person can be suppressed compared with a case in which the light guide part 120 is composed of a hard material.

Note that the light guide part 120 does not necessarily need to be formed of an elastic body as described above. The light guide part 120 may be composed of a hard material.

Moreover, according to the embodiment, the second surface 121 is formed of a curved plane in which the protrusion height is the highest at the part of the second opening 123. Effects to be described below are obtained by forming the second surface 121 in this manner.

The skin 401 gets contact with the second surface 121 from a direction different from the Z-axis direction depending on the shape of the arm 400 of the wearing person, the wearing method, or body motion of the wearing person. FIG. 12 is a diagram illustrating a state of the contact between the light guide part 120 and the skin 401 in a case in which the contact direction tilts around the X-axis. FIG. 13 is a diagram illustrating a state of the contact between the light guide part 120 and the skin 401 in a case in which the contact direction tilts around the Y-axis.

According to the embodiment, the second surface 121 is formed of a curved plane in which the protrusion height is the highest at the part of the second opening 123. Therefore, even if the contact direction tilts around the X-axis or the contact direction tilts around the Y-axis, the part of the second opening 123 (top part and vicinity thereof) serves as a fulcrum as illustrated in FIGS. 12 and 13, and the tight contact between the peripheral part of the second opening 123 and the skin can be kept. Thus, it is possible to block light that is emitted from the light emitting element 111 and is reflected or scattered by the skin 401 to travel toward the light receiving element 112, and the pulse wave can be detected without the deterioration of the detection accuracy.

FIG. 14 is a diagram that compares the related art and the present embodiment and illustrates the S/N ratio of the pulse wave waveform when a user who wears the wearable device 1000 shakes the arm 400 in various directions.

As illustrated in FIG. 14, the sensor 100 of the embodiment obtains a high S/N ratio compared with the P sensor 200 in any case.

Modification Example: Regarding Adjustment Mechanism

A modification example of the embodiment will be described below.

As is apparent also from the description made thus far, a structure in which the light guide part 120 is typically in contact with the skin is desirable. An adjustment mechanism thereof will be described with FIG. 15. Note that the adjustment mechanism can be referred to also as a pressing adjustment mechanism or a height adjustment mechanism of the sensor substrate 110. In this adjustment mechanism 130, an elastic part 132 that can expand and contract by a pressure like a sponge is disposed in a casing 131 that is a support member.

When the band 1003 is tightened, the light guide part 120 is pushed up by the skin, and the sensor substrate 110 is pushed up. As a result, the sponge contracts in the thickness direction whereas the sensor substrate 110 is pushed out toward the skin. Thus, the light guide part 120 typically abuts against the skin.

Figure 15:
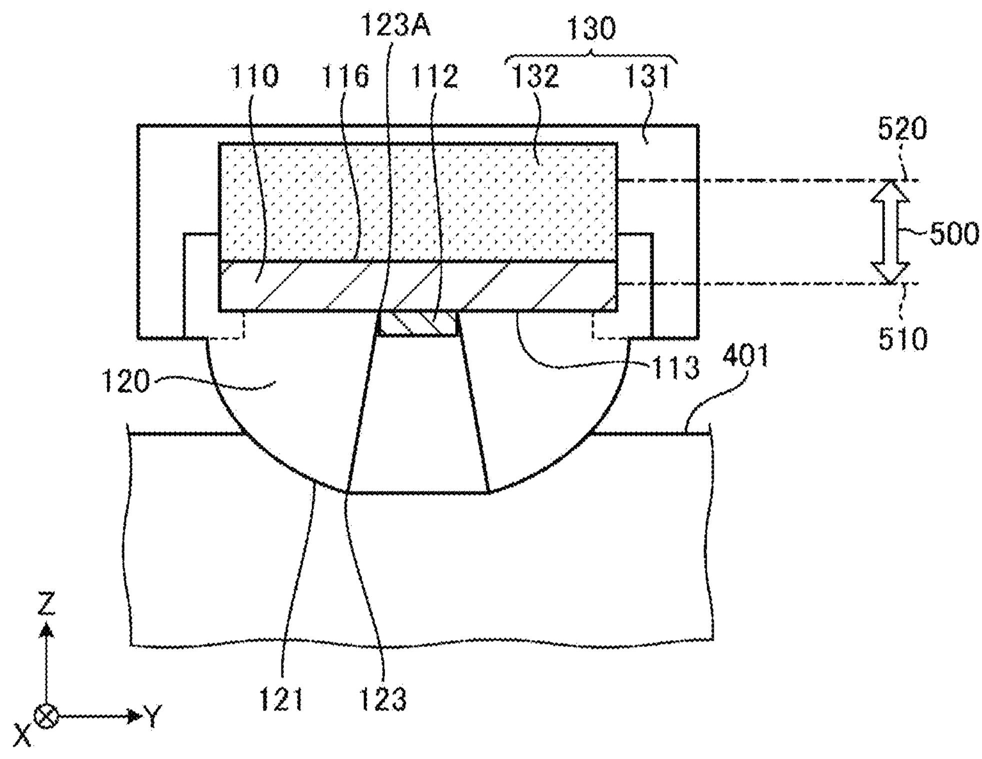
FIG. 15 is a diagram for explaining an adjustment mechanism according to a modification example of the embodiment.

FIG. 15 is a diagram for explaining this adjustment mechanism 130.

For example, a support member (here, casing) having an internal space that can house the sensor substrate 110 and the elastic part 132 is prepared. Part of the casing 131 is opened by an opening. The periphery of this opening has steps to allow the folded-back parts 128 to be fitted thereto. The light guide part 120 integrated with the sensor substrate 110 is fitted into the opening with these steps. Thereby, the sensor substrate 110 to which the light guide part 120 is fixed is disposed in the casing 131 with the first surface 113 as the mounting surface oriented outward. Furthermore, the adjustment mechanism 130 is disposed on the back surface of the sensor substrate 110 exposed from the light guide part 120. In the diagram, the elastic part 132 composed of a resin like a sponge is disposed. However, an elastic part composed of a metal, such as a spring, may be employed.

The light guide part 120 to which the sensor substrate 110 is fitted is disposed with an extremely-thin gap from an inner wall forming the internal space of the casing, and is disposed movably in the thickness direction of the casing. Thus, the light guide part 120 is pushed up in the upward direction in FIG. 15 when being attached to the arm. As a result, the sponge contracts. On the other hand, due to the contraction of the sponge, that is, a restoring force thereof, the sensor substrate 110 is pressed downward, so that the light guide part 120 typically abuts against the skin.

For example, in FIG. 15, the sensor substrate 110 is allowed to move from a lower-limit position 510 located at the center of the sensor substrate 110 to an upper-limit position 520. In a state in which the light guide part 120 is pressed against the skin 401, the elastic part 132 flexibly gets deformed and contracts like a spring, and the sensor substrate 110 moves in a range 500. Furthermore, the elastic part 132 pushes the sensor substrate 110 in the direction from the third surface 116 toward the first surface 113 by the force for restoration. Conversely, in a state in which the light guide part 120 is not pressed against the skin 401, the sensor substrate 110 is fixed at the lower-limit position 510 of the range 500 by the force of pushing by the elastic part 132.

Figure 16:
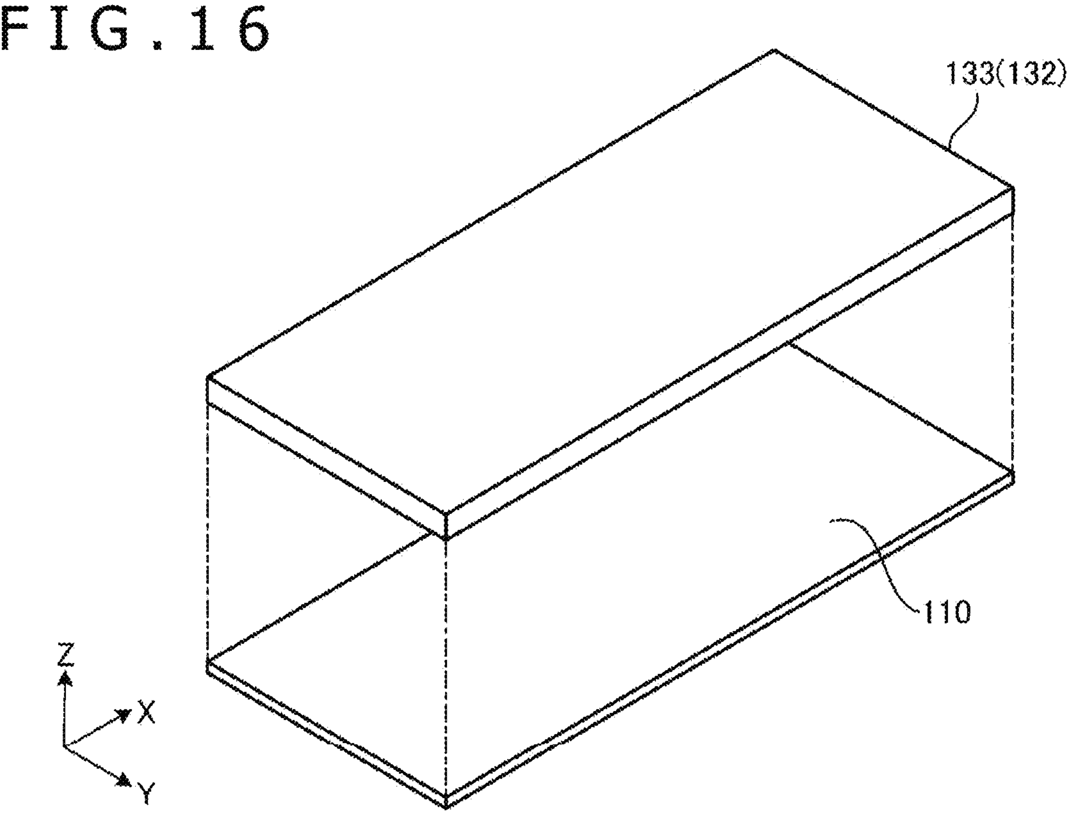
FIG. 16 is a diagram for explaining one example of the shape of a sponge as an elastic part according to the modification example of the embodiment.
Figure 17:
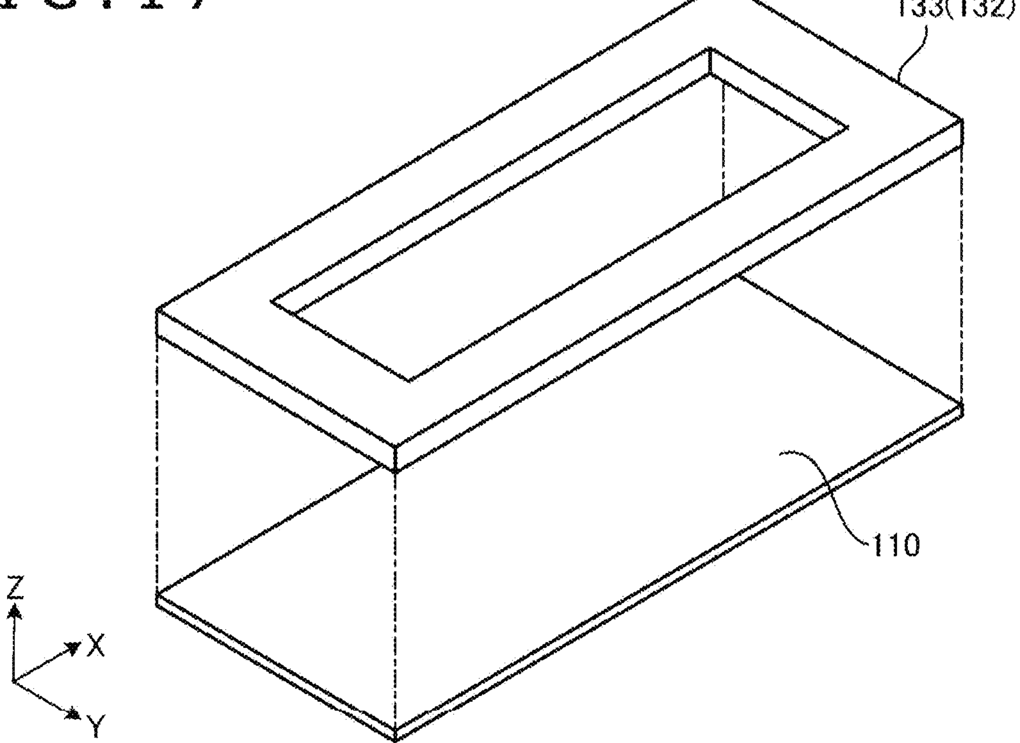
FIG. 17 is a diagram for explaining another example of the shape of the sponge as the elastic part according to the modification example of the embodiment.
Figure 18:
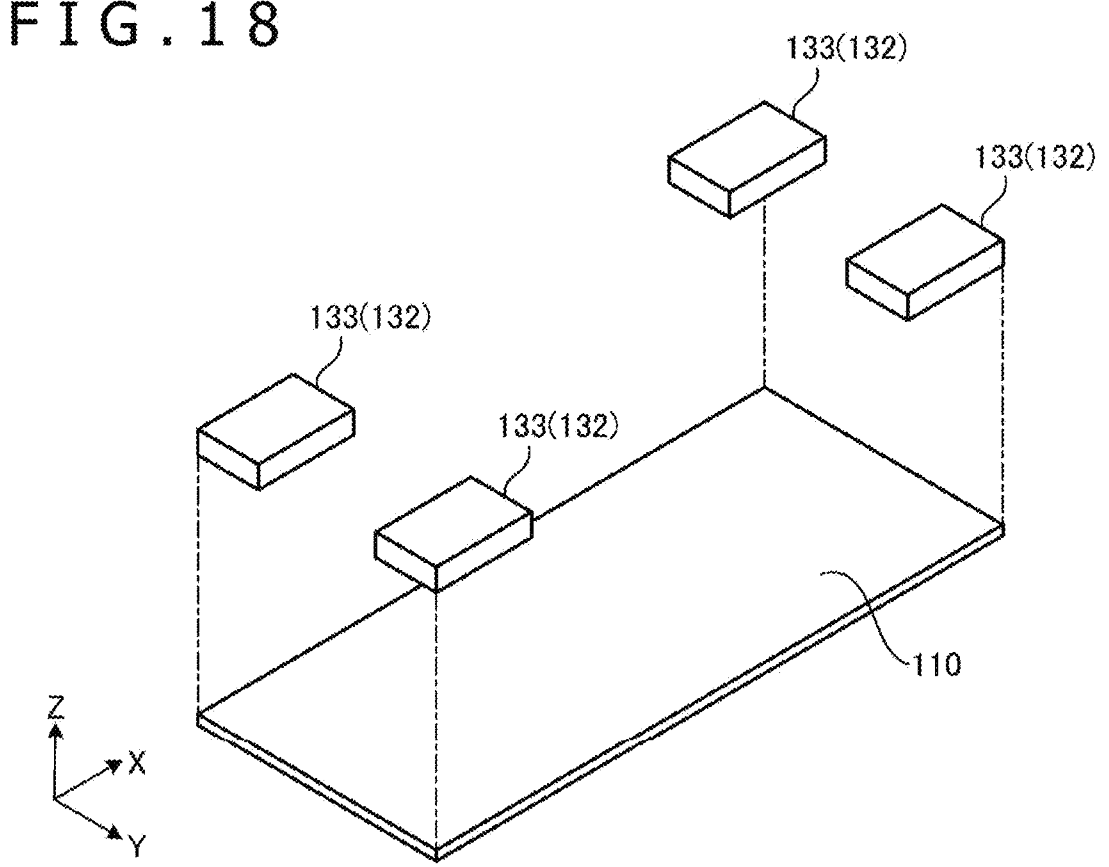
FIG. 18 is a diagram for explaining yet another example of the shape of the sponge as the elastic part according to the modification example of the embodiment.

The elastic part 132 may be a flat plate-shaped sponge 133 having an area substantially equivalent to that of the third surface 116 as illustrated in FIG. 16. Alternatively, the elastic part 132 may be the flat plate-shaped sponge 133 in which a hole is bored at the center as illustrated in FIG. 17. Alternatively, the elastic part 132 may be the flat plate-shaped sponge 133 divided into a plurality of pieces as illustrated in FIG. 18. Note that, in FIG. 18, the flat plate-shaped sponge 133 is divided into four pieces, and the pieces are disposed at four corners of the third surface 116, so that the four corners of the third surface 116 can be pushed. Note that the elastic part 132 is not limited to the flat plate-shaped sponge 133. The elastic part 132 may be formed of one or more springs.

The first light guide paths 124 and the second light guide path 125 may be closed by a component through which light is transmitted. For example, a component through which light emitted by the light emitting element 111 is transmitted closes the first openings 122 and the second opening 123, and the first light guide paths 124 and the second light guide path 125 may be made hollow. Alternatively, the first light guide paths 124 and the second light guide path 125 may be filled with the component through which light emitted by the light emitting element 111 is transmitted.

Due to the closing of the first light guide paths 124 and the second light guide path 125 by the component through which light emitted by the light emitting element 111 is transmitted, adhesion of contamination to the light emitting element 111 or the light receiving element 112 can be prevented.

Even when the first light guide paths 124 and the second light guide path 125 are not closed by the component through which light emitted by the light emitting element 111 is transmitted, adhesion of contamination to the light receiving element 112 can be prevented by disposing a translucent cover that covers the opening 123A or the second opening 123.

The present disclosure contains subject matter related to that disclosed in Japanese Priority Patent Application JP 2022-013623 filed in the Japan Patent Office on Jan. 31, 2022, the entire content of which is hereby incorporated by reference.

What is claimed is:

1. A pulse wave detection device comprising:

a sensor substrate having a mounting surface and a back surface;

a light receiving element disposed on the mounting surface of the sensor substrate;

a light emitting element disposed on the mounting surface separately from the light receiving element; and a light guide part having, on a side of the mounting surface of the sensor substrate, a first opening that surrounds the light receiving element, a second opening that corresponds to the first opening and is provided in a curved surface of the light guide part, a third opening that surrounds the light emitting element, a fourth opening that corresponds to the third opening and is provided in the curved surface of the light guide part, a first light guide path having a reflective surface that couples the first opening with the second opening, and a second light guide path having a reflective surface that couples the third opening with the fourth opening.

2. The pulse wave detection device according to claim 1, further comprising a fitting part provided on a side of abutting against the sensor substrate in the light guide part, wherein the light guide part is fixed to the sensor substrate by the fitting part.

3. The pulse wave detection device according to claim 2, further comprising a casing partly opened by an opening, wherein the sensor substrate to which the light guide part is fixed is disposed in the opening of the casing in such a manner that the mounting surface is oriented toward an outside of the casing, and the casing houses an elastic part between a bottom part of an internal space of the casing and the sensor substrate.

4. The pulse wave detection device according to claim 1, wherein the light guide part is formed of an elastic body and is capable of expansion and contraction.

5. The pulse wave detection device according to claim 1, wherein glossing treatment has been executed for the reflective surface of the first light guide path and the reflective surface of the second light guide path.

6. The pulse wave detection device according to claim 1, wherein the first opening or the second opening is covered by a translucent cover.

* * * * *